(12) United States Patent
Kim et al.

(10) Patent No.: US 10,685,219 B2
(45) Date of Patent: Jun. 16, 2020

(54) SIGN LANGUAGE RECOGNITION SYSTEM AND METHOD

(71) Applicant: UNIVERSITY INDUSTRY FOUNDATION, YONSEI UNIVERSITY WONJU CAMPUS, Wonju-si (KR)

(72) Inventors: Young Ho Kim, Wonju-si (KR); Seong Jung Kim, Wonju-si (KR); Han Soo Lee, Wonju-si (KR); Jong Man Kim, Wonju-si (KR); Min Jo, Wonju-si (KR); Eun Kyoung Choi, Wonju-si (KR); Soon Jae Ahn, Wonju-si (KR); Young Jae Jeong, Wonju-si (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 95 days.

(21) Appl. No.: 16/073,441

(22) PCT Filed: Oct. 17, 2016

(86) PCT No.: PCT/KR2016/011650
§ 371 (c)(1),
(2) Date: Jul. 27, 2018

(87) PCT Pub. No.: WO2017/131318
PCT Pub. Date: Aug. 3, 2017

(65) Prior Publication Data
US 2019/0073525 A1 Mar. 7, 2019

(30) Foreign Application Priority Data

Jan. 27, 2016 (KR) .................. 10-2016-0010230
Apr. 11, 2016 (KR) .................. 10-2016-0043914

(51) Int. Cl.
*G06K 9/00* (2006.01)
*G06F 1/16* (2006.01)
(Continued)

(52) U.S. Cl.
CPC ........ *G06K 9/00355* (2013.01); *A61B 5/0488* (2013.01); *G06F 1/1694* (2013.01);
(Continued)

(58) Field of Classification Search
CPC .......... A61B 5/0488; A61B 2562/0219; A61B 5/1116; A61B 5/7264; A61B 5/04012;
(Continued)

(56) References Cited

U.S. PATENT DOCUMENTS

2003/0166996 A1  9/2003  Kim et al.

FOREIGN PATENT DOCUMENTS

JP  2004157994  6/2004
KR  20080028084  3/2008
(Continued)

*Primary Examiner* — Sam Bhattacharya
(74) *Attorney, Agent, or Firm* — Cantor Colburn LLP

(57) ABSTRACT

Provided is a sign language recognition system, and the sign language recognition system includes an acquisition unit configured to acquire an electromyogram signal of a user from a sensor measurement device worn around an arm of the user, an extraction unit configured to extract a muscle active section from the electromyogram signal to detect a sign language gesture of the user, a producing unit configured to produce a first feature vector by performing signal processing to the muscle active section, a search unit configured to search a signal corresponding to the first feature vector in a database, and an output unit configured to output a text corresponding to the searched signal.

19 Claims, 10 Drawing Sheets

(51) Int. Cl.
  *A61B 5/0488*   (2006.01)
  *G06F 3/01*     (2006.01)
  *G09B 21/00*    (2006.01)
  *A61B 5/11*     (2006.01)
  *A61B 5/00*     (2006.01)
  *A61B 5/04*     (2006.01)

(52) U.S. Cl.
  CPC .............. *G06F 3/015* (2013.01); *G06F 3/017* (2013.01); *G09B 21/009* (2013.01); *A61B 5/04012* (2013.01); *A61B 5/1116* (2013.01); *A61B 5/7264* (2013.01); *A61B 2562/0219* (2013.01)

(58) Field of Classification Search
  CPC ........ G06F 3/015; G06F 3/017; G06F 1/1694; G09B 21/009; G06K 9/00355
  See application file for complete search history.

(56) References Cited

FOREIGN PATENT DOCUMENTS

| | | |
|---|---|---|
| KR | 20120064922 | 6/2012 |
| KR | 20140143922 | 12/2014 |
| KR | 101551424 | 9/2015 |
| KR | 20150115522 | 10/2015 |

FIG.5
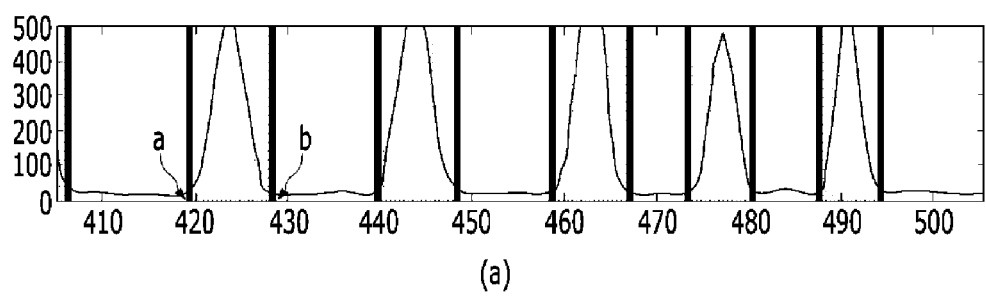
(a)
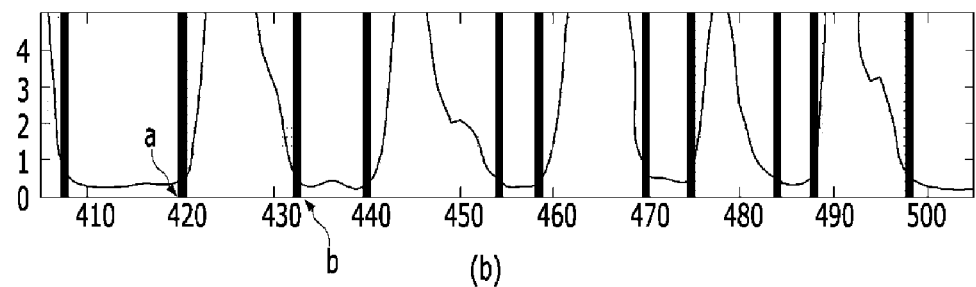
(b)

NEURAL NETWORK MAPPING

SIGN LANGUAGE RECOGNITION SYSTEM AND METHOD

TECHNICAL FIELD

The present disclosure relates to a sign language recognition system and method.

BACKGROUND

Sign language or finger language is a method of communication for deaf and dumb people using body or hand gestures instead of spoken language and employs shapes made with fingers or arms, their orientation or movement, facial expression, or lip movement to convey ideas.

Conventional sign language recognition systems or finger language recognition systems are configured to take pictures of gestures in sign language or finger language with a camera and analyze the gestures, and, thus, they are time consuming and unhandy to carry.

Further, in recent years, a technology of recognizing sign language or finger language using sign language gloves has been suggested. However, there is a limitation in wearing the sign language gloves for a long time due to sweat from hands or the like and the sign language gloves need to be taken off to perform daily activities, such as face washing, likely to cause contact with foreign substance.

The background technology of the present disclosure is disclosed in Korean Patent No. 10-1551424 (registered on Sep. 2, 2015).

DISCLOSURE OF THE INVENTION

Problems to be Solved by the Invention

The present disclosure is conceived to solve the above-described problem of the conventional technology and provides a sign language recognition system which is easy to carry without interference with daily activities and a sign language recognition method.

Further, the present disclosure is conceived to solve the above-described problem of the conventional technology and provides a sign language recognition system which can clearly identify gestures in sign language and finger language in a short time and a sign language recognition method.

However, problems to be solved by the present disclosure are not limited to the above-described problems. There may be other problems to be solved by the present disclosure.

Means for Solving the Problems

As a technical means for solving the above-described technical problems, a sign language recognition system according to an embodiment of the present disclosure may include an acquisition unit configured to acquire an electromyogram signal of a user from a sensor measurement device worn around an arm of the user, an extraction unit configured to extract a muscle active section from the electromyogram signal to detect a sign language gesture of the user, a producing unit configured to produce a first feature vector by performing signal processing to the muscle active section, a search unit configured to search a signal corresponding to the first feature vector in a database, and an output unit configured to output a text corresponding to the searched signal.

Further, the acquisition unit may receive electromyogram signals according to a gesture of straightening the user's wrist through multiple electrode channels included in the sensor measurement device, identify an electrode channel having a maximum root mean square value from among the multiple electrode channels on the basis of the electromyogram signals received from the respective multiple electrode channels, and rearrange the multiple electrode channels included in the sensor measurement device in consideration of a position of the identified electrode channel in the sensor measurement device.

Furthermore, if the acquisition unit acquires an inertial signal from an inertial measurement unit included in the sensor measurement device, the extraction unit may extract a motion section of the arm from the inertial signal and the producing unit may produce a second feature vector by performing signal processing to the motion section, and the search unit may search a signal corresponding to an integrated feature vector in the database on the basis of the integrated feature vector obtained by integrating the first feature vector and the second feature vector.

Moreover, the acquisition unit may compute an orientation initial value of the inertial measurement unit and an orientation value of the inertial measurement unit according to real-time receipt of the inertial signal using the acquired inertial signal and arithmetically operate conversion values of a roll angle, a pitch angle, and a yaw angle of the inertial measurement unit using a reference vector determined on the basis of the orientation initial value and a movement vector determined on the basis of the orientation value.

Further, the extraction unit may extract the muscle active section and the motion section by applying a Teager-Kaiser Energy Operator (TKEO) to each of the electromyogram signals received from the respective multiple electrode channels included in the sensor measurement device and the inertial signal acquired from the inertial measurement unit.

Furthermore, the extraction unit may extract a section having a predetermined muscle activity threshold value or more from the electromyogram signals as the muscle active section and a section having a predetermined motion threshold value or more from the inertial signal as the motion section.

Moreover, the producing unit may produce the first feature vector by arithmetically operating a root mean square value of the electromyogram signals for the respective multiple electrode channels included in the sensor measurement device on the basis of the muscle active section, and the second feature vector by arithmetically operating conversion values of a roll angle, a pitch angle, and a yaw angle of the inertial measurement unit on the basis of the motion section and then applying a high-pass filter.

Further, the first feature vector and the second feature vector may be resampled by normalizing time data.

Furthermore, the search unit may perform the search using a neural network formed through learning of a specific sign language gesture.

Moreover, the sensor measurement device may include an armband to be worn around the arm, multiple electrodes arranged at intervals along an inner circumference of the armband to face the arm, and an inertial measurement unit provided in one area of the sensor measurement device, and the inertial measurement unit may include a three-axis accelerometer, a three-axis angular velocity sensor, and a three-axis magnetometer.

Meanwhile, a sign language recognition method according to an embodiment of the present disclosure may include acquiring an electromyogram signal of a user from a sensor measurement device worn around an arm of the user, extracting a muscle active section from the electromyogram signal to detect a sign language gesture of the user, producing a first feature vector by performing signal processing to the muscle active section, searching a signal corresponding to the first feature vector in a database, and outputting a text corresponding to the searched signal.

Further, the acquiring process may include receiving electromyogram signals according to a gesture of straightening the user's wrist through multiple electrode channels included in the sensor measurement device, identifying an electrode channel having a maximum root mean square value from among the multiple electrode channels on the basis of the electromyogram signals received from the respective multiple electrode channels, and rearranging the multiple electrode channels included in the sensor measurement device in consideration of a position of the identified electrode channel in the sensor measurement device.

Furthermore, if an inertial signal is acquired from an inertial measurement unit included in the sensor measurement device in the acquiring process, the extracting process may include extracting a motion section of the arm from the inertial signal and the producing process may include producing a second feature vector by performing signal processing to the motion section, and the searching process may include searching a signal corresponding to an integrated feature vector in the database on the basis of the integrated feature vector obtained by integrating the first feature vector and the second feature vector.

Moreover, the acquiring process may include computing an orientation initial value of the inertial measurement unit and an orientation value of the inertial measurement unit according to real-time receipt of the inertial signal using the acquired inertial signal, and arithmetically operating conversion values of a roll angle, a pitch angle, and a yaw angle of the inertial measurement unit using a reference vector determined on the basis of the orientation initial value and a movement vector determined on the basis of the orientation value.

Further, the extracting process may include extracting the muscle active section and the motion section by applying a Teager-Kaiser Energy Operator (TKEO) to each of the electromyogram signals received from the respective multiple electrode channels included in the sensor measurement device and the inertial signal acquired from the inertial measurement unit.

Furthermore, the extracting process may include extracting a section having a predetermined muscle activity threshold value or more from the electromyogram signals as the muscle active section, and a section having a predetermined motion threshold value or more from the inertial signal as the motion section.

Moreover, the producing process may include producing the first feature vector by arithmetically operating a root mean square value of the electromyogram signals for the respective multiple electrode channels included in the sensor measurement device on the basis of the muscle active section, and producing the second feature vector by arithmetically operating conversion values of a roll angle, a pitch angle, and a yaw angle of the inertial measurement unit on the basis of the motion section and then applying a high-pass filter.

Further, the first feature vector and the second feature vector may be resampled by normalizing time data.

Furthermore, the searching process may include performing the search using a neural network formed through learning of a specific sign language gesture.

Moreover, the sensor measurement device may include an armband to be worn around the arm, multiple electrodes arranged at intervals along an inner circumference of the armband to face the arm, and an inertial measurement unit provided in one area of the sensor measurement device, and the inertial measurement unit may include a three-axis accelerometer, a three-axis angular velocity sensor, and a three-axis magnetometer.

The above-described embodiments are provided by way of illustration only and should not be construed as liming the present disclosure. Besides the above-described embodiments, there may be additional embodiments described in the accompanying drawings and the detailed description.

Effects of the Invention

According to the above-described means for solving the problems, it is possible to rapidly and accurately recognize an idea through a sign language gesture by acquiring an electromyogram signal of a user and an inertial signal from a sensor measurement device worn around an arm of the user, producing a feature vector of a sign language gesture of the user on the basis of the electromyogram signal and the inertial signal, and outputting a text corresponding to the produced feature vector in a database.

According to the above-described means for solving the problems, an electromyogram signal and an inertial signal according to a user's sign language gesture can be measured through a sensor measurement device which can be worn around the user's arm, and the user's sign language gesture can be identified on the basis of the measured electromyogram signal and inertial signal. Thus, it is possible to provide a sign language recognition system which is easy to carry without interference with daily activities and a sign language recognition method.

According to the above-described means for solving the problems, a user's sign language gesture can be recognized in consideration of an electromyogram signal acquired from an electromyogram sensor and a three-dimensional angle of the user's arm acquired through an inertial measurement unit. Thus, it is possible to more accurately recognize the user's sign language gesture.

BRIEF DESCRIPTION OF THE DRAWINGS

FIG. 5 is a diagram illustrating an example of detecting a muscle active section and a motion section in the sign language recognition system according to an embodiment of the present disclosure;

BEST MODE FOR CARRYING OUT THE INVENTION

Figure 1:
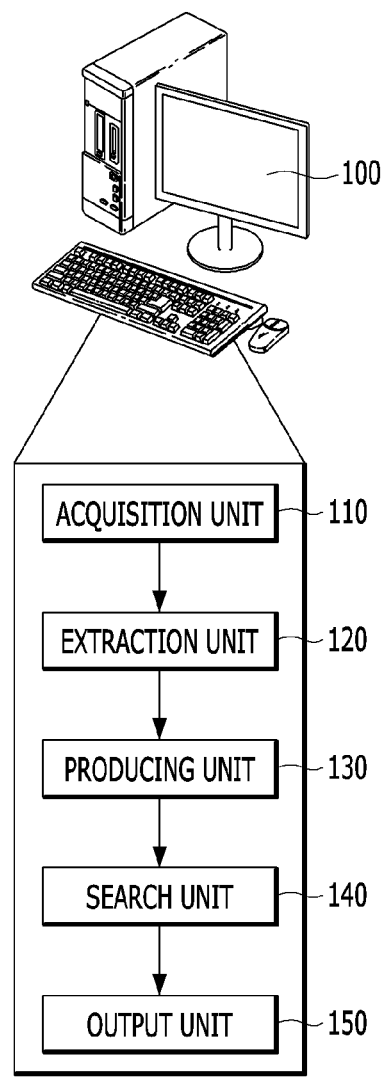
FIG. 1 is a diagram schematically illustrating the entire configuration of a sign language recognition system according to an embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to, or indirectly connected or coupled to" another element via still another element.

Through the whole document, the terms "on", "above", "on an upper end", "below", "under", and "on a lower end" that are used to designate a position of one element with respect to another element include both a case that the one element is touch to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The present disclosure relates to a sign language recognition system and method for recognizing a sign language gesture and a finger language gesture using an electromyogram signal and an inertial signal.

Figure 2:
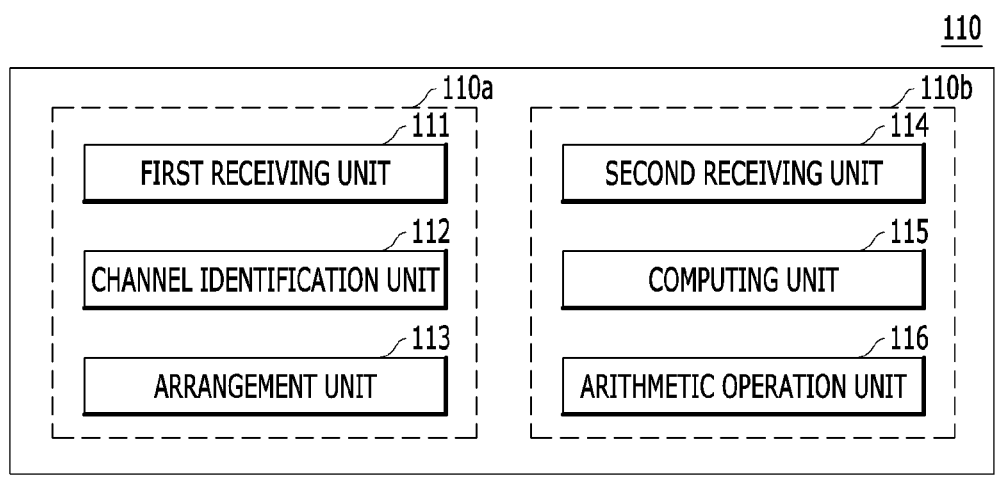
FIG. 2 is a diagram schematically illustrating a configuration of an acquisition unit in the sign language recognition system according to an embodiment of the present disclosure.

FIG. 1 is a diagram schematically illustrating the entire configuration of a sign language recognition system according to an embodiment of the present disclosure, and FIG. 2 is a diagram schematically illustrating a configuration of an acquisition unit in the sign language recognition system according to an embodiment of the present disclosure.

Referring to FIG. 1, a sign language recognition system 100 according to an embodiment of the present disclosure may include an acquisition unit 110, an extraction unit 120, a producing unit 130, a search unit 140, and an output unit 150.

The acquisition unit 110 may acquire an electromyogram signal and an inertial signal of a user from a sensor measurement device worn around an arm of the user. The sensor measurement device used in the present disclosure to acquire an electromyogram signal and an inertial signal can be more easily understood with reference to FIG. 3.

Figure 3:
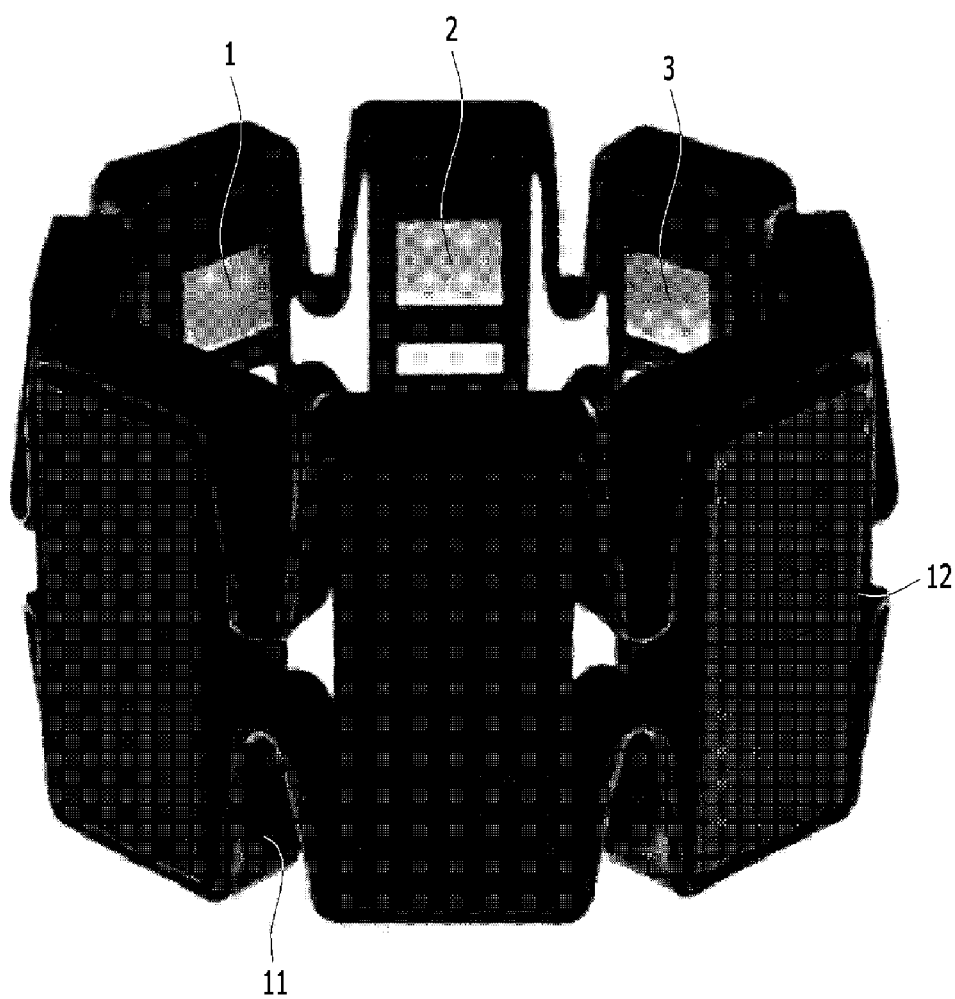
FIG. 3 is a diagram illustrating a sensor measurement device used in the sign language recognition system according to an embodiment of the present disclosure.

FIG. 3 is a diagram illustrating a sensor measurement device used in the sign language recognition system according to an embodiment of the present disclosure.

Referring to FIG. 3, the sensor measurement device 10 according to an embodiment of the present disclosure can be worn around an arm of a user. Particularly, the sensor measurement device 10 can be worn around a forearm between the wrist and the elbow and may also be worn around an upper arm between the elbow and the shoulder.

The sensor measurement device 10 may include an armband 11, multiple electrodes (for example, a first electrode 1, a second electrode 2, a third electrode 3, . . . ), and an inertial measurement unit (IMU) 12. The armband 11 may be a band to be worn around the user's arm. The armband 11 may be formed of a material which can be extended or contracted depending on a thickness of the user's body part around which the sensor measurement device 10 is to be worn. The multiple electrodes 1, 2, 3, . . . may be arranged at intervals along an inner circumference of the armband 11 to face the arm of the user. The multiple electrodes 1, 2, 3, . . . may be electromyogram electrodes. The inertial measurement unit 12 may be provided in one area of the sensor measurement device 10. The inertial measurement unit 12 may include a three-axis accelerometer, a three-axis gyroscope, and a three-axis magnetometer.

Further, the sensor measurement device 10 may include a controller (not illustrated). The sensor measurement device 10 may measure electromyogram signals of the user through the multiple electrodes 1, 2, 3, . . . on the basis of a control signal of the controller. Furthermore, the sensor measurement device 10 may acquire an inertial signal through the inertial measurement unit 12 on the basis of a control signal of the controller. The sign language recognition system 100 according to an embodiment of the present disclosure can accurately identify a sign language gesture of the user on the basis of the measured electromyogram signals and the measured inertial signal.

Also, the controller may transmit the electromyogram signals measured through the multiple electrodes and the inertial signal measured through the inertial measurement unit 12 to the sign language recognition system 100 via wireless communication such as Bluetooth, near field communication (NFC), etc. Thus, the acquisition unit 110 of the sign language recognition system 100 may acquire the electromyogram signals and inertial signal of the user from the sensor measurement device 10.

Referring to FIG. 2, the acquisition unit 110 may roughly include a first acquisition unit 110a for calibration of electromyogram signal and a second acquisition unit 110b for calibration of inertial signal. The first acquisition unit 110a may include a first receiving unit 111, a channel identification unit 112, and an arrangement unit 113, and the second acquisition unit 110b may include a second receiving unit 114, a computing unit 115, and an arithmetic operation unit 116.

The calibration refers to a process of adjusting the electromyogram signals measured through the multiple electrodes 1, 2, 3, . . . and the inertial signal measured through the inertial measurement unit 12 to a predetermined standard depending on a feature (or scale) of a subject (i.e., user). Thus, the sign language recognition system 100 according to an embodiment of the present disclosure can more accurately analyze the electromyogram signals and inertial signal measured through the sensor measurement device 10 in consideration of features of the user.

The sign language recognition system 100 according to an embodiment of the present disclosure can calibrate the electromyogram signals measured through the sensor measurement device 10 using the first receiving unit 111, the channel identification unit 112, and the arrangement unit 113.

The first receiving unit 111 may receive electromyogram signals according to a gesture of straightening the user's wrist through multiple electrode channels included in the sensor measurement device 10. The multiple electrode channels refer to channels corresponding to each of the multiple electrodes 1, 2, 3, . . . .

The channel identification unit 112 can identify an electrode channel having a maximum root mean square (RMS) value from among the multiple electrode channels on the basis of the electromyogram signals received from the respective multiple electrode channels.

The channel identification unit 112 can identify a position of an electrode channel having a maximum root mean square value from among the multiple electrode channels by comparing the electromyogram signals received from the respective multiple electrode channels.

The position of the electrode channel having a maximum root mean square value may refer a position corresponding to a position of a wrist extensor bundle. Therefore, the channel identification unit 112 can detect the position of the wrist extensor bundle by identifying the position of the electrode channel having a maximum root mean square value.

The position of the electrode channel identified by the channel identification unit 112 may be stored in a database (not illustrated).

The arrangement unit 113 may rearrange the multiple electrode channels included in the sensor measurement device 10 in consideration of the position of the electrode channel identified by the channel identification unit 112 for measuring uniformly electromyogram signals. The user may wear the sensor measurement device 10 and then perform initial calibration of the electrode channels through the rearrangement and thus can set the acquisition unit 110 to acquire an electromyogram signal corresponding to the wrist extensor bundle associated with the gesture of straightening the wrist with high accuracy.

Further, the sign language recognition system 100 can calibrate the inertial signal measured through the sensor measurement device 10 using the second receiving unit 114, the computing unit 115, and the arithmetic operation unit 116.

The second receiving unit 114 may receive an inertial signal according to a motion of the user through the inertial measurement unit 12 included in the sensor measurement device 10.

The computing unit 115 may compute an orientation initial value of the inertial measurement unit 12 using the inertial signal measured through the inertial measurement unit 12. The orientation initial value of the inertial measurement unit 12 may include a roll angle (phi, ø) corresponding to roll rotation, a pitch angle (theta, θ) corresponding to pitch rotation, and a yaw angle (psi, ψ)) corresponding to yaw rotation.

Hereinafter, examples of computing an orientation initial value of the inertial measurement unit 12 will be described with reference to Equation 1 to Equation 8.

The computing unit 115 may determine an initial value of roll angle of the inertial measurement unit 12 and an initial value of pitch angle of the inertial measurement unit 12 using an acceleration signal for x-axis of the inertial measurement unit 12, an acceleration signal for y-axis of the inertial measurement unit 12, and an acceleration signal for z-axis of the inertial measurement unit 12. The following Equation 1 and Equation 2 show examples of determining an initial value of roll angle and an initial value of pitch angle by the computing unit 115.

$$\begin{bmatrix} a_x \\ a_y \\ a_z \end{bmatrix} = C_n^b \begin{bmatrix} 0 \\ 0 \\ g \end{bmatrix} \begin{bmatrix} -g\sin\theta \\ g\cos\theta\sin\phi \\ g\cos\phi\cos\theta \end{bmatrix} \quad \text{[Equation 1]}$$

Referring to Equation 1, the computing unit 115 may use $a_x$ which is an acceleration signal for x-axis of the inertial measurement unit 12, $a_y$ which is an acceleration signal for y-axis of the inertial measurement unit 12, $a_z$ which is an acceleration signal for z-axis of the inertial measurement unit 12, and g which is the acceleration of gravity vector to obtain the roll angle (ø) and the pitch angle (θ). In this case, $C_n^b$ may refer to a conversion matrix and can be expressed as shown in Equation 2.

$$C_n^b = C_3^b(\phi)C_2^b(0)C_n^b(\psi) \quad \text{[Equation 2]}$$

$$= \begin{bmatrix} \cos\theta\cos\psi & \cos\theta\sin & -\sin\theta \\ \cos\psi\sin\phi\sin\theta - \cos\phi\sin\psi & \sin\phi\sin\theta\sin\psi + \cos\phi\cos\psi & \cos\theta\sin\phi \\ \cos\phi\cos\psi\sin\theta + \sin\phi\sin\psi & \cos\phi\sin\theta\sin\psi - \cos\psi\sin\phi & \cos\phi\cos\theta \end{bmatrix}$$

Referring to Equation 2, the conversion matrix $C_n^b$ may refer to a navigation coordinate system showing conversion from reference coordinate system to body coordinate system. As shown in Equation 2, the conversion matrix $C_n^b$ may include conversion of roll angle, conversion of pitch angle, and conversion of yaw angle as components, and the conversion of roll angle, the conversion of pitch angle, and the conversion of yaw angle can be expressed as $$C_3^b(\phi) = \begin{bmatrix} 1 & 0 & 0 \\ 0 & \cos\phi & \sin\phi \\ 0 & -\sin\phi & \cos\phi \end{bmatrix}, C_2^3(\theta) = \begin{bmatrix} \cos\theta & 0 & -\sin\theta \\ 0 & 1 & 0 \\ \sin\theta & 0 & \cos\theta \end{bmatrix}, \text{and}$$

$$C_n^2(\psi) = \begin{bmatrix} \cos\psi & \sin\psi & 0 \\ -\sin\psi & \cos\psi & 0 \\ 0 & 0 & 1 \end{bmatrix},$$

respectively.

Referring to Equation 1 and Equation 2, Since the z axis among the three axes of the x axis, y axis, and z axis coincides with the gravity acceleration direction, the calculation unit 115 determines the z axis value to be 1 (g: gravity acceleration) and the remaining two axes x axis, y Each axis can be set to zero. Through this, the calculation unit 115 can calculate the values of a roll angle ($\phi$) and pitch angle ($\theta$). The computing unit 115 may determine the computed roll angle ($\phi$) and pitch angle ($\theta$) as an initial value of roll angle and an initial value of pitch angle, respectively. Meanwhile, a yaw angle can be expressed by psi ($\psi$).

The computing unit 115 may use a geomagnetic signal for x-axis of the inertial measurement unit 12, a geomagnetic signal for y-axis of the inertial measurement unit 12, and a geomagnetic signal for z-axis of the inertial measurement unit 12 to obtain an initial value of yaw angle of the inertial measurement unit 12. Hereinafter, examples of determining an initial value of yaw angle by the computing unit 115 will be described with reference to Equation 3 to Equation 8.

Referring to Equation 3, the computing unit 115 may use $m_x$ which is a geomagnetic signal for x-axis of a first sensor 110, $m_y$ which is a geomagnetic signal for y-axis of the first sensor, $m_z$ which is a geomagnetic signal for z-axis of the first sensor 110, a conversion matrix $C_n^b$, and geomagnetic vectors $m_1$, $m_2$, and $m_3$ to obtain an initial value of yaw angle ($\psi$).

$$\begin{bmatrix} m_x \\ m_y \\ m_z \end{bmatrix} = C_n^b \begin{bmatrix} m_1 \\ m_2 \\ m_3 \end{bmatrix} \quad \text{[Equation 3]}$$

Meanwhile, $C_n^b$ ($C_n^b = C_3^b(\phi)C_2^3(\theta)C_{11}^2(\psi)$) can be expressed by $C_1$ associated with the roll angle and the pitch angle and $C_2$ associated with the yaw angle as shown in Equation 4, and Equation 1 can be converted into Equation 5 and Equation 6.

$$C_1 = \begin{bmatrix} \cos\theta & 0 & -\sin\theta \\ \sin\phi\sin\theta & \cos\phi & \sin\phi\cos\theta \\ \cos\phi\sin\theta & -\sin\phi & \cos\phi\cos\theta \end{bmatrix}, \quad \text{[Equation 4]}$$

$$C_2 = \begin{bmatrix} \cos\psi & \sin\psi & 0 \\ -\sin\psi & \cos\psi & 0 \\ 0 & 0 & 1 \end{bmatrix}$$

$$\begin{bmatrix} m_x \\ m_y \\ m_z \end{bmatrix} = C_1 C_2 \begin{bmatrix} m_1 \\ m_2 \\ m_3 \end{bmatrix} \quad \text{[Equation 5]}$$

$$C_1^{-1} \begin{bmatrix} m_x \\ m_y \\ m_z \end{bmatrix} = C_2 \begin{bmatrix} m_1 \\ m_2 \\ m_3 \end{bmatrix} \quad \text{[Equation 6]}$$

If $C_1$ and $C_2$ of Equation 4 are substituted into Equation 6, Equation 7 and Equation 8 can be derived. The computing unit 115 may obtain an initial value of yaw angle by substituting the geomagnetic signals $m_x$, $m_y$, and $m_z$, at a roll angle ($\phi$) of 0 and a pitch angle ($\theta$) of 0, and the geomagnetic vectors $m_1$, $m_2$, and $m_3$ into Equation 8.

$$\begin{bmatrix} \cos\theta & \sin\phi\sin\theta & \cos\phi\sin\theta \\ 0 & \cos\phi & -\sin\phi \\ -\sin\theta & \sin\phi\sin\theta & \cos\phi\cos\theta \end{bmatrix} \begin{bmatrix} m_x \\ m_y \\ m_z \end{bmatrix} = \begin{bmatrix} \cos\psi & \sin\psi & 0 \\ -\sin\psi & \cos\psi & 0 \\ 0 & 0 & 1 \end{bmatrix} \begin{bmatrix} m_1 \\ m_2 \\ m_3 \end{bmatrix} \quad \text{[Equation 7]}$$

$$\begin{bmatrix} \cos\theta\, m_x + \sin\phi\sin\theta\, m_y + \cos\phi\sin\theta\, m_z \\ \cos\phi\, m_y - \sin\phi\, m_z \\ -\sin\theta\, m_x + \sin\phi\sin\theta\, m_y + \cos\phi\cos\theta\, m_z \end{bmatrix} = \begin{bmatrix} \cos\psi\, m_1 + \sin\psi\, m_2 \\ -\sin\psi\, m_1 + \cos\psi\, m_2 \\ m_3 \end{bmatrix} \quad \text{[Equation 8]}$$

As such, the computing unit 115 can compute orientation initial values of the inertial measurement unit 12, i.e., an initial value of roll angle (phi, $\psi$), an initial value of pitch angle (theta, $\theta$), and an initial value of yaw angle (psi, $\psi$) of the inertial measurement unit 12, using Equation 1 to Equation 8. The computing unit 115 can determine a reference vector $\text{Vector}_0$ on the basis of computed operation initial values. By determining the reference vector, the initial calibration of the inertial signal can be completed.

Then, the computing unit 115 receives an inertial signal measured through the inertial measurement unit 12 in real time and thus can compute an orientation value of the inertial measurement unit 12 according to real-time receipt of the inertial signal. That is, the computing unit 115 may compute operation initial values and then arithmetically operate an orientation value of the inertial measurement unit 12 in real time using Equation 1 to Equation 8. The computing unit 115 may determine a movement vector $\text{Vector}_{move}$ using the real-time arithmetically operated orientation value.

The arithmetic operation unit 116 may use the reference vector $\text{Vector}_0$ determined on the basis of the orientation initial values of the inertial measurement unit 12 and the movement vector $\text{Vector}_{move}$ determined on the basis of the orientation value to arithmetically operate conversion values of the roll angle, the pitch angle, and the yaw angle of the inertial measurement unit 12. More details are as follows.

Firstly, the arithmetic operation unit 116 may compute quaternion elements during rotation from the reference vector $\text{Vector}_0$ to the movement vector $\text{Vector}_{move}$. The quaternion elements can be expressed as shown in Equation 9.

$$q = [Q1, Q2, Q3, Q4] \quad \text{[Equation 9]}$$
$$= \left[\cos\frac{\theta}{2}, r_x\sin\frac{\theta}{2}, r_y\sin\frac{\theta}{2}, r_z\sin\frac{\theta}{2}\right]$$

The arithmetic operation unit 116 may apply a Half-Way Quaternion Solution for operation of quaternion elements using inner and outer products between two vectors to compute the quaternion elements.

Accordingly, an angle component Q1 between the reference vector $\text{Vector}_0$ and the movement vector $\text{Vector}_{move}$ can be induced by multiplying inner products of the reference vector $\text{Vector}_0$ and the movement vector $\text{Vector}_{move}$ by the magnitude of vector, as shown in Equation 10.

$$Q1 = \text{Vector}_0 \cdot \text{Vector}_{move} + |\text{Vector}_0||\text{Vector}_{move}| \quad \text{[Equation 10]}$$

Further, x, y, and z components Q2, Q3, and Q4 of a rotation axis can be induced using outer products of x, y, and z vectors between the reference vector $\text{Vector}_0$ and the movement vector $\text{Vector}_{move}$, and can be expressed as shown in Equation 11.

$$Q2 = \text{Vector}_{0\_x} \times \text{Vector}_{move\_x}$$
$$Q3 = \text{Vector}_{0\_y} \times \text{Vector}_{move\_y}$$
$$Q4 = \text{Vector}_{0\_z} \times \text{Vector}_{move\_z} \quad \text{[Equation 11]}$$

Then, the arithmetic operation unit 116 may arithmetically operate conversion values of the roll angle, the pitch angle, and the yaw angle of the inertial measurement unit 12 on the basis of Quaternion-Euler conversion, and the conversion values can be expressed as shown in Equation 12.

$$\begin{bmatrix} \phi \\ \theta \\ \psi \end{bmatrix} = \begin{bmatrix} \tan^{-1}\frac{2(Q1*Q2+Q3*Q4)}{1-2(Q2^2+Q3^2)} \\ \sin^{-1}2(Q1*Q3-Q4*Q2) \\ \tan^{-1}\frac{2(Q1*Q4+Q2*Q3)}{1-2(Q3^2+Q4^2)} \end{bmatrix} \quad \text{[Equation 12]}$$

The extraction unit 120 may extract a muscle active section from an electromyogram signal acquired by the acquisition unit 110 to detect a sign language gesture of the user. Further, the extraction unit 120 may extract a motion section from an inertial signal acquired by the acquisition unit 110. An example of extracting a muscle active section will be described first.

The extraction unit 120 may apply a band-pass filter to the electromyogram signal acquired by the acquisition unit 110 before extracting a muscle active section. For example, the extraction unit 120 may apply a band-pass filter of 10 Hz to 450 Hz to the acquired electromyogram signals. Further, the extraction unit 120 may apply an analog-digital converter (ADC) to the acquired electromyogram signal.

The extraction unit 120 may extract a muscle active section by applying a Teager-Kaiser Energy Operator (TKEO) to electromyogram signals received from the respective multiple electrode channels. Further, the extraction unit 120 may extract a section having a predetermined muscle activity threshold value or more from the electromyogram signal acquired by the acquisition unit 110 as a muscle active section.

The Teager-Kaiser Energy Operator (TKEO) refers to a signal processing method capable of extracting a muscle active section from a small gesture such as a finger gesture and can detect the muscle activity of a finger motion having a low signal to noise ratio (SNR). The TKEO is well known to those skilled in the art. Therefore, hereinafter, an example of application of the TKEO to the sign language recognition system according to an embodiment of the present disclosure will be described rather than the TKEO itself.

Figure 4:
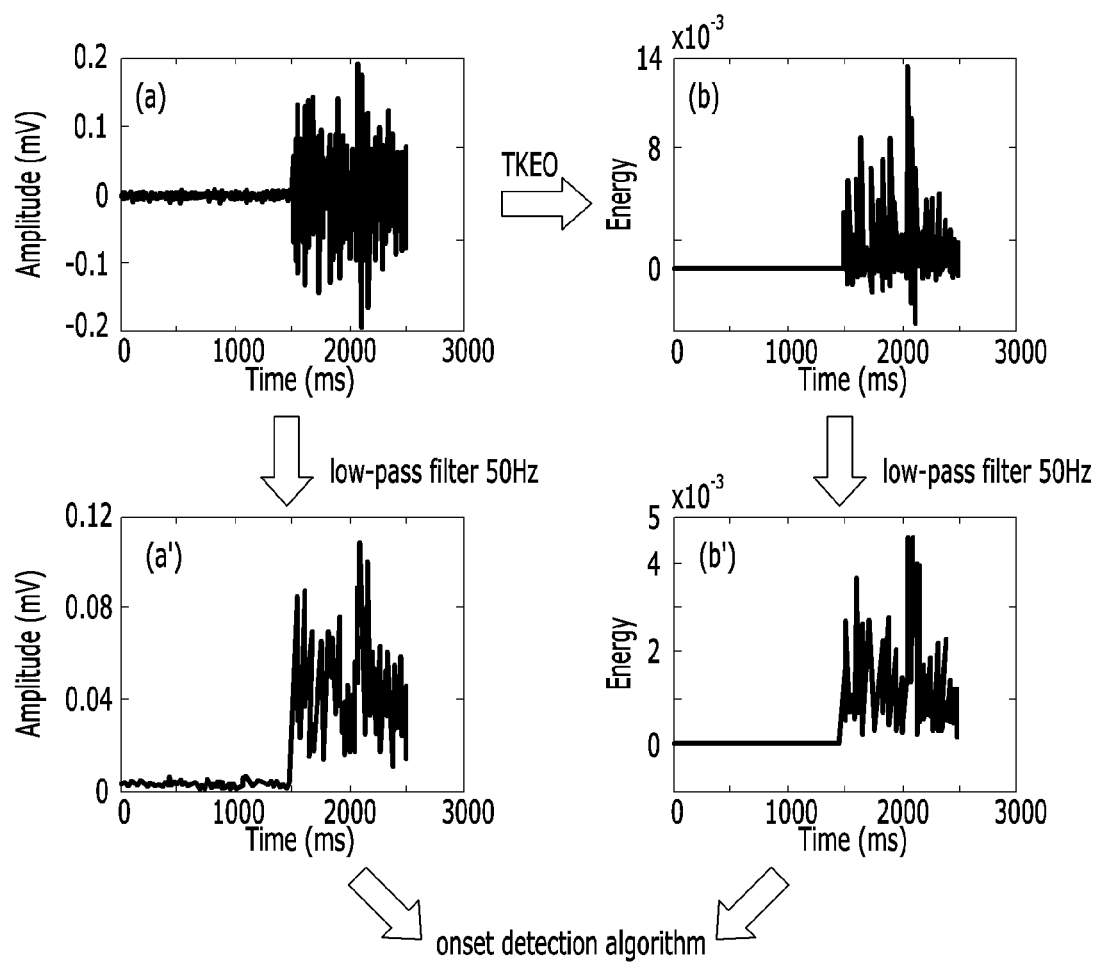
FIG. 4 is a diagram illustrating an example of a TKEO used in the sign language recognition system according to an embodiment of the present disclosure.

FIG. 4 is a diagram illustrating an example of a TKEO used in the sign language recognition system according to an embodiment of the present disclosure.

Referring to FIG. 4, for example, FIG. 4 portions (a) shows a graph of a signal to which the TKEO is not applied and FIG. 4 portions (b) shows a graph of the signal of FIG. 4 portions (a) after applying the TKEO. FIG. 4 portions (a') shows a graph after applying a low-pass filter of 50 Hz to FIG. 4 portions (a), and FIG. 4 portions (b') shows a graph after applying a low-pass filter of 50 Hz to FIG. 4 portions (b). It can be seen that a signal to noise ratio (SNR) of FIG. 4 portions (b') is greatly increased compared with that of FIG. 4 portions (a') and thus the probability of misdetection in a muscle active section is decreased.

The extraction unit 120 may apply the TEKO to each of the electromyogram signals received from the respective multiple electrode channels to extract a muscle active section.

If the TKEO is applied to an electromyogram signal received from the sensor measurement device 10, it can be expressed as shown in Equation 13.

$$\psi\_emg[x(n)] = emg^2(n) - emg(n+1)emg(n-1) \quad \text{[Equation 13]}$$

Then, the extraction unit 120 can synthesize data (electromyogram signals) for each channel (i.e., multiple electrode channels) to which applied with the TKEO, and it can be expressed as shown in Equation 14.

$$u_{emg(n)} = \psi_{emg1[x(n)]} + \psi_{emg2[x(n)]} + \cdots + \psi_{emg8[x(n)]} \quad \text{[Equation 14]}$$

Herein, $\psi_{emg1[x(n)]}$ represents an electromyogram signal (EMG) for channel 1, $\psi_{emg2[x(n)]}$ represents an electromyogram signal for channel 2, and $\psi_{emg8[x(n)]}$ represents an electromyogram signal for channel 8.

Then, the extraction unit 120 can compute a root mean square (RMS) value of composite data obtained by composing the data for all the respective channels. A root mean square value $U_{RMS\_EMG}$ of the composite data can be expressed as shown in Equation 15.

$$U_{RMS\_EMG} = \sqrt{\frac{\sum_{n=0}^{N-1} u\_emg^2(n)}{N}} \quad \text{[Equation 15]}$$

Herein, N represents a window width, U_emg(n) represents composite data of TKEO-applied electromyogram signals, and $U_{RMS\_EMG}$ represents RMS data of the composite electromyogram signals (i.e., composite data).

The extraction unit 120 may produce the root mean square value of the composite data and then perform rectification for acquiring an absolute value of an electromyogram signal.

The extraction unit 120 may acquire a linear envelope signal simplified from the electromyogram signal by applying a band-pass filter, a low-pass filter and the TKEO and performing rectification and output of root mean square value of the composite data to the electromyogram signal acquired by the acquisition unit 110. Then, the extraction unit 120 may extract a muscle active section on the basis of the linear envelope signal. An example of extracting a muscle active section can be more easily understood with reference to FIG. 5.

FIG. 5 is a diagram illustrating an example of detecting a muscle active section and a motion section in the sign language recognition system according to an embodiment of the present disclosure. FIG. 5 portions (a) shows an example of detecting a muscle active section and FIG. 5 portions (b) shows an example of detecting a motion section. Hereinafter, the example of detecting a muscle active section will be described first with reference to FIG. 5 portions (a), and the example illustrated in FIG. 5 portions (b) will be described later.

A threshold value for detecting a muscle active section may be set in advance by user input. The threshold value may be defined as "Average of Baseline+J*Standard deviation". Herein, Baseline represents an electromyogram signal measured when the user is relaxed, and j represents a constant value.

The threshold value is a scale for determining whether or not the muscle of a subject is in a muscle active state, and if an electromyogram signal measured through the sensor measurement device 10 is equal to or higher than the threshold value, the muscle activity may be determined as turned on and if the electromyogram signal is lower than the threshold value, the muscle activity may be determined as turned off.

In FIG. 5 portions (a), a point a indicates a point where the muscle activity is turned on and a point b indicates a point where the muscle activity is turned off. Therefore, a section between the point a and the point b may be considered as a muscle active section.

The extraction unit 120 may extract a muscle activity cycle by setting a point where an electromyogram signal acquired by the acquisition unit 110 is increased to be equal to or higher than the threshold value as a muscle activity ON point (for example, point a) and a point where the electromyogram signal is decreased to be equal to or lower than the threshold value as a muscle activity OFF point (for example, point b).

If a muscle active section is detected from the electromyogram signal acquired by the acquisition unit 110, the extraction unit 120 may determine that the user makes a sign language gesture or a finger language gesture and then stop the measurement of electromyogram signals. If the muscle active section is detected, the extraction unit 120 may deactivate the acquisition unit 110 and activate the producing unit 130. If the muscle active section is not detected, the extraction unit 120 may deactivate the producing unit 130 and activate the acquisition unit 110. Further, the measurement of electromyogram signals by the sensor measurement device 10 may be stopped by user input.

Meanwhile, hereinafter, an example of extracting a motion section on the basis of an inertial signal will be described.

The extraction unit 120 may apply a band-pass filter to an inertial signal acquired by the acquisition unit 110 before extracting a motion section from the inertial signal. Thus, the extraction unit 120 may extract signal spectra of an accelerometer, an angular velocity sensor, and a magnetometer included in the inertial measurement unit 12.

Then, the extraction unit 120 may compute a signal vector magnitude (SVM) of an acceleration signal on the basis of the inertial signal acquired through the inertial measurement unit 12, and the signal vector magnitude can be expressed as shown in Equation 16.

$$SVM = \sqrt{Acc_x^2 + Acc_y^2 Acc_z^2}$$ [Equation 16]

Then, the extraction unit 120 may apply the TKEO to the SVM of the acceleration signal, and it can be expressed as shown in Equation 17.

$$\psi\_acc[x(n)] = SVM^2(n) - SVM(n+1)SVM(n-1)$$ [Equation 17]

Then, the extraction unit 120 may compute a root mean square (RMS) value of Equation 17, and it can be expressed as shown in Equation 18.

$$U_{RMS\_IMU} = \sqrt{\frac{\sum_{n=0}^{N-1} \psi\_acc^2(n)}{N}}$$ [Equation 18]

Herein, N represents a window width, $\psi\_acc(n)$ represents a TKEO-applied acceleration signal, and $U_{RMS\_acc}$ represents RMS data of the TKEO-applied acceleration signal.

Then, the extraction unit 120 can extract a motion section which is measured when the user makes a sign language gesture from the inertial signal on the basis of the RMS data of the TKEO-applied acceleration signal. An example of extracting a motion section can be more easily understood with reference to FIG. 5 portions (b).

Referring to FIG. 5 portions (b), the extraction unit 120 may determine a time when an inertial signal measured through the sensor measurement device 10 is increased to be equal to or higher than a predetermined threshold value as a motion on state and a time when the inertial signal is decreased to be lower than the threshold value as a motion off state.

In FIG. 5 portions (a), the point a indicates a point where a motion is turned on and the point b indicates a point where the motion is turned off. Therefore, the section between the point a and the point b may be considered as a motion section.

The extraction unit 120 may extract a motion cycle by setting a point where an inertial signal acquired by the acquisition unit 110 is increased to be equal to or higher than the threshold value as a motion ON point (for example, point a) and a point where the inertial signal is decreased to be equal to or lower than the threshold value as a motion OFF point (for example, point b).

If a motion section is detected from the inertial signal acquired by the acquisition unit 110, the extraction unit 120 may determine that the user makes a sign language gesture or a finger language gesture and then stop the measurement of inertial signals. If the motion section is detected, the extraction unit 120 may deactivate the acquisition unit 110 and activate the producing unit 130. If the motion section is not detected, the extraction unit 120 may deactivate the producing unit 130 and activate the acquisition unit 110. Further, the measurement of inertial signals by the sensor measurement device 10 may be stopped by user input.

Through the above-described processes, the extraction unit 120 may extract a section having a predetermined muscle activity threshold value or more from an electromyogram signal as a muscle active section and a section having a predetermined motion threshold value or more from an inertial signal as a motion section.

Then, the producing unit 130 may produce a first feature vector of the sign language gesture of the user by performing signal processing to each of the muscle active section and the motion section extracted by the extraction unit 120, and a second feature vector of the sign language gesture of the user by performing signal processing to the motion section. An example of producing the first feature vector will be described first.

The producing unit 130 may produce the first feature vector by arithmetically operating a root mean square (RMS) value of electromyogram signals for the respective multiple electrode channels included in the sensor measurement device 10 on the basis of an electromyogram signal included in the muscle active section. In this case, the producing unit 130 may produce the first feature vector of the sign language gesture of the user in consideration of the position of the electrode channel identified by the channel identification unit 112. Further, the producing unit 130 may remove data of other sections except the muscle active section from the electromyogram signal.

The producing unit 130 may arithmetically operate a root mean square $FRMS_c$ of electromyogram signals for the respective channels in the muscle active section using the following Equation 19.

$$FRMS_C = \left[\sqrt{\frac{\sum_{n=0}^{N-1} u^2(\tau)}{N}}\right]_C$$ [Equation 19]

Herein, C represents a channel number for electrode and τ represents a muscle active section. For example, a channel number for the first electrode 1 may be 1 and a channel number for the second electrode 2 may be 2.

The producing unit 130 may produce the first feature vector by normalizing time data on the basis of the root mean square $FRMS_c$ produced using Equation 19. The first feature vector may be resampled by normalizing time data to be easily compared with feature vectors stored in a database (not illustrated). Hereinafter, an example of producing the second feature vector will be described.

The producing unit 130 may remove data of other sections except the motion section from the inertial signal. For example, the producing unit 130 may remove all of roll, pitch, and yaw data except a section from which a gesture is detected through an acceleration signal.

Further, the producing unit 130 may apply a Euler high-pass filter to the extracted motion section. More specifically, the producing unit 130 may arithmetically operate the conversion values of the roll angle, the pitch angle, and the yaw angle of the inertial measurement unit 12 on the basis of the extracted motion section and then apply the high-pass filter to produce the second feature vector. For example, the producing unit 130 may apply a high-pass filter of 0.1 Hz and thus fix offsets of the roll, pitch, and yaw data to 0 and thus produce a second feature vector. In this case, the first feature vector may be resampled by normalizing time data with the producing unit 130 to be easily compared with feature vectors stored in the database (not illustrated).

Further, the producing unit 130 may produce an integrated feature vector(Feature) by integrating the first feature vector produced on the basis of the electromyogram signal and the second feature vector produced on the basis of the inertial signal using Equation 20.

$$\text{Feature}=\text{FRMS}_1,\text{FRMS}_2,\ldots,\text{FRMS}_C,\text{roll},\text{pitch},\text{yawl} \qquad [\text{Equation 20}]$$

Herein, Feature represents a feature vector of a sign language gesture or a finger language gesture of the user, $\text{FRMS}_1$ represents a root mean square value of an electromyogram signal acquired through a channel for the first electrode 1 in the muscle active section, and $\text{FRMS}_2$ represents a root mean square value of an electromyogram signal acquired through a channel for the second electrode 2 in the muscle active section. Further, roll, pitch, and yaw represent root mean square values of an inertial signal (i.e., IMU signal) acquired through the inertial measurement unit 12.

Figure 6:
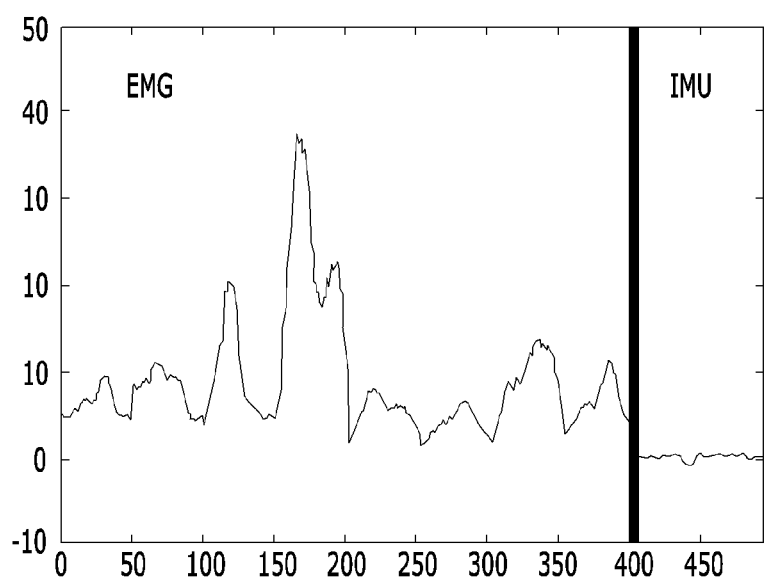
FIG. 6 shows a graph of integrated feature vectors produced through a sign language recognition system according to an embodiment of the present disclosure.

FIG. 6 shows a graph of integrated feature vectors calculated through a sign language recognition system according to an embodiment of the present disclosure, and for example, an integrated feature vector of a sign language gesture of the user produced by the producing unit 130 may be as shown in the graph of FIG. 6.

The search unit 140 may search a signal corresponding to the integrated feature vector in the database on the basis of the integrated feature vector produced in the producing unit 130 by integrating the first feature vector and the second feature vector.

In this case, the search unit 140 may perform the search using a neural network formed through learning of a specific sign language gesture or finger language gesture. An example of the neural network is illustrated in FIG. 7.

Figure 7:
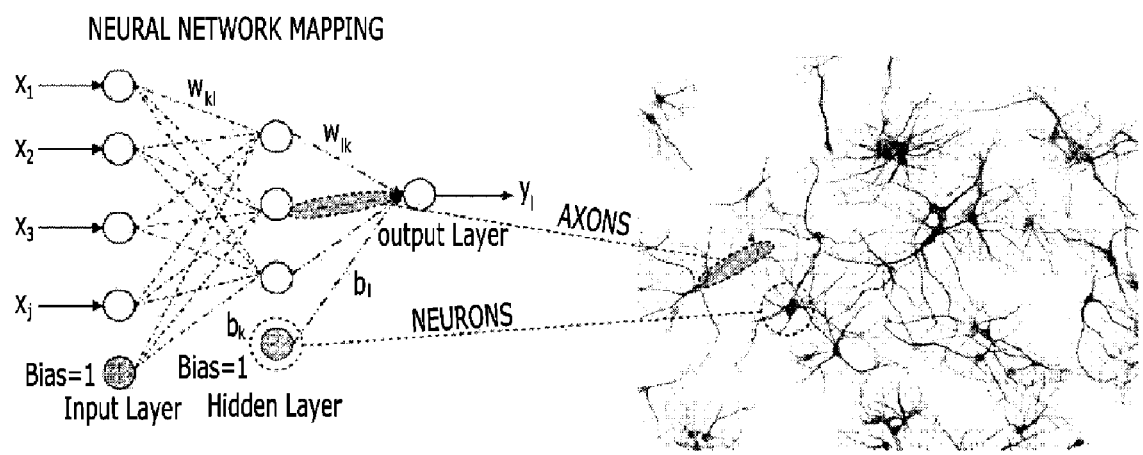
FIG. 7 is a diagram illustrating an example of a neural network used in the sign language recognition system according to an embodiment of the present disclosure.

FIG. 7 is a diagram illustrating an example of a neural network used in the sign language recognition system according to an embodiment of the present disclosure.

Referring to FIG. 7, the search unit 140 can quickly and accurately search a signal corresponding to the integrated feature vector produced by the producing unit 130 in the database (not illustrated) through a pattern recognition method based on a neural network. To this end, the search unit 140 may determine a parameter (W, bias) of a neural network to maximize the probability of pattern classification through learning of a specific sign language gesture or finger language gesture.

The search unit 140 may search and extract a signal having the highest similarity with the integrated feature vector from among signals included in the database. This can be more easily understood with reference to FIG. 8.

Figure 8:
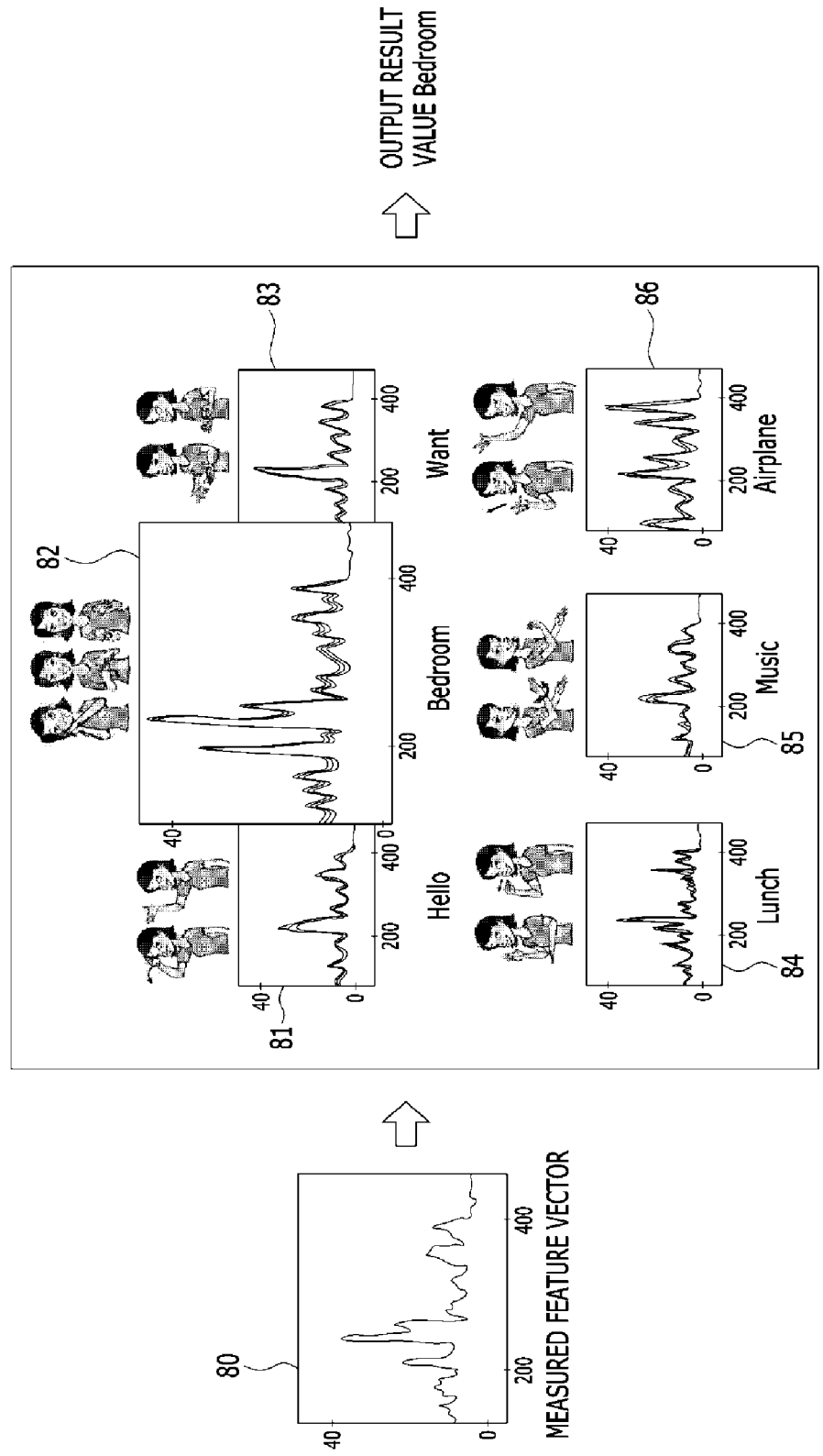
FIG. 8 is a diagram illustrating an example of detecting a signal corresponding to an integrated feature vector in the sign language recognition system according to an embodiment of the present disclosure.

FIG. 8 is a diagram illustrating an example of detecting a signal corresponding to an integrated feature vector in the sign language recognition system according to an embodiment of the present disclosure.

Referring to FIG. 8, for example, an integrated feature vector produced by the producing unit 130 can be expressed as shown in a graph 80.

The search unit 140 can search a graph corresponding to the graph 80 of the integrated feature vector produced by the producing unit 130 in the database, and signals stored in the database may be as follows. An electromyogram signal corresponding to each text (for example, word, alphabet, letter, number, consonant, vowel, etc.) and a waveform graph corresponding to an integrated feature vector of an inertial signal may be stored in the database. For example, a graph corresponding to an integrated feature vector of a sign language gesture meaning a word "Hello" may be expressed as a first graph 81. A graph corresponding to an integrated feature vector of a sign language gesture meaning a word "Bedroom" may be expressed as a second graph 82. A graph corresponding to an integrated feature vector of a sign language gesture meaning a word "Want" may be expressed as a third graph 83. A graph corresponding to an integrated feature vector of a sign language gesture meaning a word "Lunch" may be expressed as a fourth graph 84. A graph corresponding to an integrated feature vector of a sign language gesture meaning a word "Music" may be expressed as a fifth graph 85. A graph corresponding to an integrated feature vector of a sign language gesture meaning a word "Airplane" may be expressed as a sixth graph 86.

The search unit 140 may search a signal corresponding to the graph 80 of the integrated feature vector in the database and extract the second graph 82 as a search result.

Then, the output unit 150 may output the word "Bedroom" as a text corresponding to the second graph 82 searched by the search unit 140.

The output unit 150 may output a text corresponding to the signal searched by the search unit 140 through a display screen or a speaker.

Figure 9:
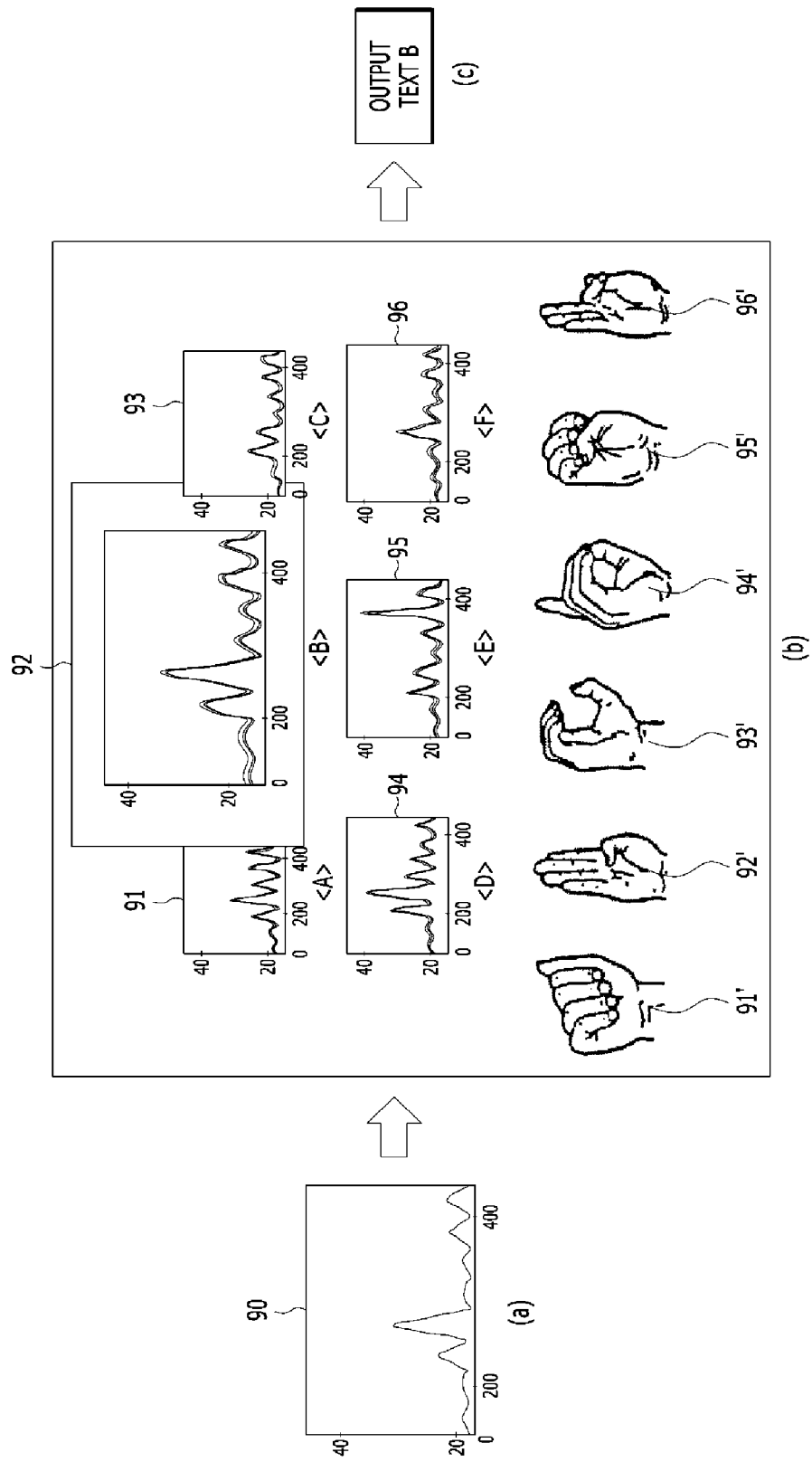
FIG. 9 is a diagram illustrating an example of detecting a signal corresponding to a feature vector for a finger language gesture in the sign language recognition system according to an embodiment of the present disclosure.

FIG. 9 is a diagram illustrating an example of detecting a signal corresponding to a feature vector for a finger language gesture in the sign language recognition system according to an embodiment of the present disclosure.

Referring to FIG. 9, FIG. 9 portions (a) shows a graph 90 of an integrated feature vector produced by the producing unit 130.

FIG. 9 portions (b) shows examples of signals stored in the database, and more details are as follows. A waveform graph of an electromyogram signal corresponding to each text (for example, alphabet, letter, number, consonant, vowel, etc.) may be stored in the database. For example, an electromyogram signal graph corresponding to a finger language gesture 91' meaning a text "A" may be expressed as a first graph 91. An electromyogram signal graph corresponding to a finger language gesture 92' meaning a text "B" may be expressed as a second graph 92. An electromyogram signal graph corresponding to a finger language gesture 93' meaning a text "C" may be expressed as a third graph 93. An electromyogram signal graph corresponding to a finger language gesture 94' meaning a text "D" may be expressed as a fourth graph 94. An electromyogram signal graph corresponding to a finger language gesture 95' meaning a text "E" may be expressed as a fifth graph 95. An electromyogram signal graph corresponding to a finger language gesture 96' meaning a text "F" may be expressed as a sixth graph 96.

The search unit 140 may search a signal corresponding to the graph 90 illustrated in FIG. 9 portions (a) in the data illustrated in FIG. 9 portions (b). The search unit 140 may extract the second graph 92 from the database as a search result for a signal corresponding to a feature vector of a finger language gesture.

Then, referring to FIG. 9 portions (c), the output unit 150 may output 'B' as a text corresponding to the search result obtained by the search unit 140.

The output unit 150 may output a text corresponding to the signal searched by the search unit 140 through a display screen or a speaker.

Figure 10:
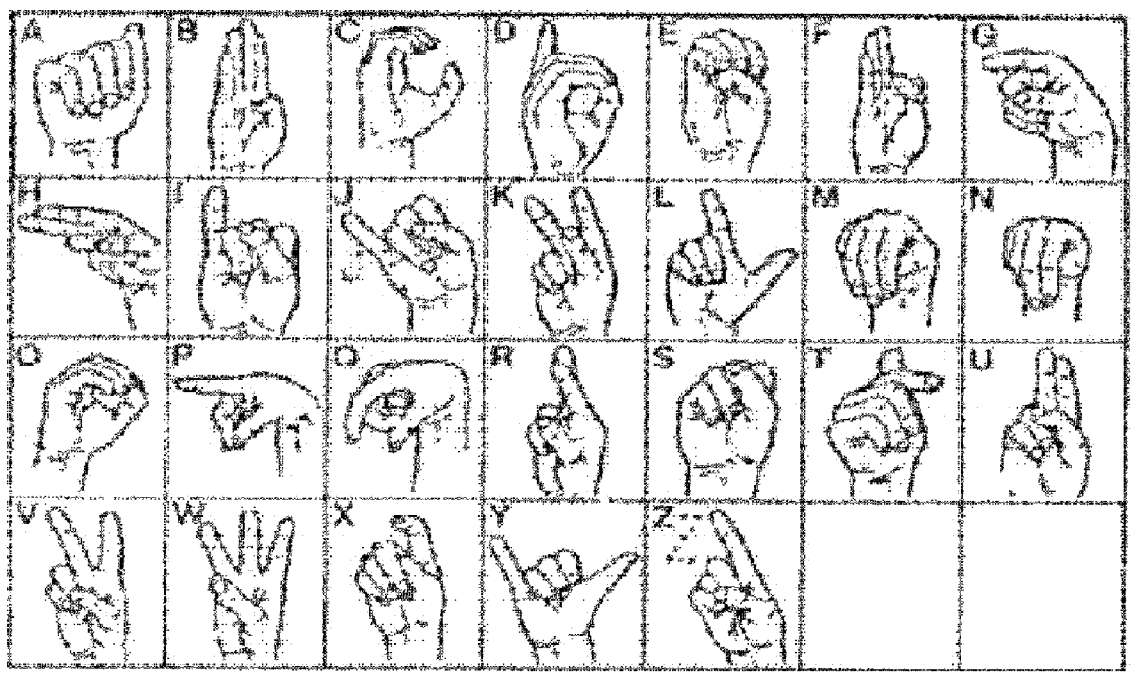
FIG. 10 is a diagram illustrating examples of finger language gestures which can be recognized by the sign language recognition system according to an embodiment of the present disclosure.

FIG. 10 is a diagram illustrating examples of finger language gestures which can be recognized by the sign language recognition system according to an embodiment of the present disclosure.

FIG. 10 illustrates examples of finger language gestures meaning A to Z, respectively. Finger language gestures may express letters, numbers, consonants, vowels, etc. as well as the alphabet, and waveforms of electromyogram signals corresponding to the respective finger language gestures may be stored in the database (not illustrated) of the sign language recognition system 100 according to an embodiment of the present disclosure.

The sign language recognition system 100 according to an embodiment of the present disclosure may be operated in a portable device, a smartphone, a personal digital assistant (PDA), a tablet computer, a notebook computer, a desktop PC, and the like, but may not be limited thereto.

The output unit 150 may output a text corresponding to the signal searched by the search unit 140 through a display screen or a speaker of a user device such as a portable device, a smartphone, a desktop PC, and the like.

Hereinafter, the flow of operations will be described briefly on the basis of the above detailed descriptions.

Figure 11:
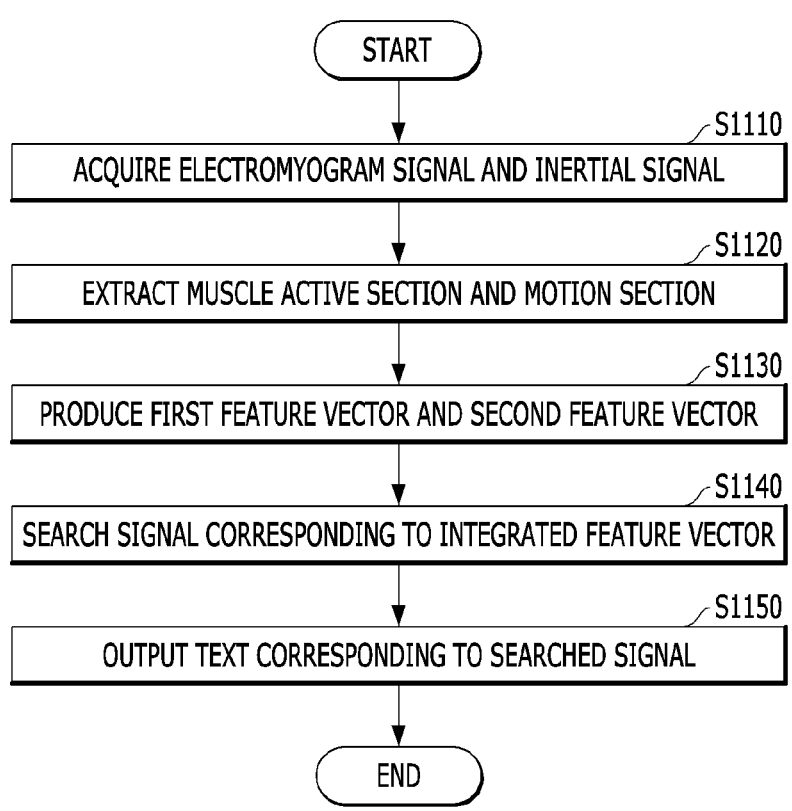
FIG. 11 is a schematic operation flowchart of a sign language recognition method according to an embodiment of the present disclosure.

FIG. 11 is a schematic operation flowchart of a sign language recognition method according to an embodiment of the present disclosure. The sign language recognition method illustrated in FIG. 11 can be performed by the sign language recognition system 100 described above. Therefore, descriptions of the sign language recognition system 100 may be identically applied to FIG. 11, even though they are omitted hereinafter.

Referring to FIG. 11, in S1110, the acquisition unit 110 may acquire an electromyogram signal and an inertial signal of a user from the sensor measurement device 10 worn around the user's arm.

In S1110, the acquisition unit 110 may receive electromyogram signals according to a gesture of straightening the user's wrist through the multiple electrode channels included in the sensor measurement device 10. Further, the acquisition unit 110 may identify an electrode channel having a maximum root mean square value from among the multiple electrode channels on the basis of the electromyogram signals received from the respective multiple electrode channels. Furthermore, the acquisition unit 110 may rearrange the multiple electrode channels included in the sensor measurement device 10 in consideration of a position of the identified electrode channel in the sensor measurement device 10 for constant sensor measurement.

Further, in S1110, the acquisition unit 110 may receive an inertial signal through the inertial measurement unit 12 included in the sensor measurement device 10. Further, the acquisition unit 110 may compute an orientation initial value of the inertial measurement unit 12 and an orientation value of the inertial measurement unit according to real-time receipt of the inertial signal using the received inertial signal. Furthermore, the acquisition unit 110 may arithmetically operate a roll angle, a pitch angle, and a yaw angle of the inertial measurement unit 12 using a reference vector determined on the basis of the orientation initial value and a movement vector determined on the basis of the orientation value.

Then, in S1120, the extraction unit 120 may extract a muscle active section from the electromyogram signal to detect a sign language gesture of the user and may extract a motion section from the inertial signal.

In S1120, the extraction unit 120 may apply the Teager-Kaiser Energy Operator (TKEO) to the electromyogram signals received from the respective multiple electrode channels to extract the muscle active section and apply the TKEO to the inertial signal received from the inertial measurement unit 12 included in the sensor measurement device 10 to extract the motion section.

Further, in S1120, the extraction unit 120 may extract a section having a predetermined muscle activity threshold value or more from the electromyogram signals as the muscle active section and a section having a predetermined motion threshold value or more from the inertial signal as the motion section.

Then, in S1130, the producing unit 130 may produce a first feature vector of the sign language gesture of the user by performing signal processing to the muscle active section extracted in S1120, and may produce a second feature vector of the sign language gesture of the user by performing signal processing to the motion section.

In S1130, the producing unit 130 may produce the first feature vector by arithmetically operating a root mean square value of the electromyogram signals for the respective multiple electrode channels included in the sensor measurement device 10 on the basis of the muscle active section and the second feature vector by applying a high-pass filter on the basis of the motion section. In this case, the first feature vector and the second feature vector may be resampled by normalizing time data. Further, the producing unit 130 may produce an integrated feature vector of the sign language gesture on the basis of the first feature vector and the second feature vector.

Then, in S1140, the search unit 140 may search a signal corresponding to the integrated feature vector in the database on the basis of the integrated feature vector produced by integrating the first feature vector and the second feature vector.

In S1140, the search unit 140 may perform the search using a neural network formed through learning of a specific sign language gesture.

Then, in S1150, the output unit 150 may output a text corresponding to the signal searched in S1140.

In the descriptions above, the processes S1110 to S1150 may be divided into additional processes or combined into fewer processes depending on an embodiment. In addition, some of the processes may be omitted and the sequence of the processes may be changed if necessary.

The sign language recognition method according to an embodiment of the present disclosure may be implemented in the form of a program command that can be performed through various computer components and may be recorded on a computer-readable storage medium. The computer-readable storage medium may include a program command, a data file, and a data structure individually or a combination thereof. The program command recorded in the medium may be specially designed and configured for the present disclosure or may be known to those skilled in a computer software field to be used. Examples of the computer-readable storage medium include magnetic media such as a hard disk, a floppy disk, and a magnetic tape, optical media such as a CD-ROM and a DVD, magneto-optical media such as a floptical disk, and a hardware device such as a ROM, a RAM, and a flash memory, that are specially configured to store and perform program commands. Examples of the program commands may include a machine code generated by a compiler and a high-level language code that can be executed in a computer using an interpreter. The hardware device may be configured as at least one software-module in order to perform the operations of the present disclosure, and vice versa.

Further, the above-described sign language recognition method may be implemented as a computer program or application stored in a storage medium and executed by a computer.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A sign language recognition system, comprising:
a sensor measurement device capable of being worn around an arm of a user, wherein the sensor measurement device includes: an armband capable of being worn around the arm; multiple electrodes arranged at intervals along an inner circumference of the armband and associated with multiple electrode channels, respectively; and an inertial measurement unit provided in an area of the sensor measurement device;
an acquisition unit configured to acquire an electromyogram signal through the multiple electrode channels according to a gesture of straightening a wrist of the user, identify an electrode channel having a maximum root mean square value among the multiple electrode channels on a basis of the electromyogram signal, and rearrange the multiple electrode channels in consideration of a position of the identified electrode channel, wherein the position of the identified electrode channel is a position corresponding to a position of a wrist extensor bundle;
an extraction unit configured to extract a muscle active section from the electromyogram signal to detect a sign language gesture of the user;
a producing unit configured to produce a first feature vector by performing signal processing to the muscle active section;
a search unit configured to search a signal corresponding to the first feature vector in a database; and
an output unit configured to output a text corresponding to the searched signal.

2. The sign language recognition system of claim 1, wherein the acquisition unit is further configured to acquire an inertial signal from the inertial measurement unit,
the extraction unit is further configured to extract a motion section of the arm from the inertial signal,
the producing unit is further configured to produce a second feature vector by performing signal processing to the motion section, and
the search unit is further configured to search a signal corresponding to an integrated feature vector in the database, wherein the integrated feature vector is obtained by integrating the first feature vector and the second feature vector.

3. The sign language recognition system of claim 2, wherein the acquisition unit is further configured to compute an orientation initial value of the inertial measurement unit and an orientation value of the inertial measurement unit according to real-time receipt of the inertial signal, and arithmetically operate conversion values of a roll angle, a pitch angle, and a yaw angle of the inertial measurement unit using a reference vector determined on a basis of the orientation initial value and a movement vector determined on a basis of the orientation value.

4. The sign language recognition system of claim 2, wherein the extraction unit is further configured to apply a Teager-Kaiser Energy Operator (TKEO) to the electromyogram signal and the inertial signal to extract the muscle active section and the motion section.

5. The sign language recognition system of claim 2, wherein the extraction unit is further configured to extract a section having a predetermined muscle activity threshold value from the electromyogram signal as the muscle active section, and a section having a predetermined motion threshold value from the inertial signal as the motion section.

6. The sign language recognition system of claim 2, wherein the producing unit is further configured to produce the first feature vector by arithmetically operating a root mean square value of the electromyogram signal for the respective multiple electrode channels included in the sensor measurement device on a basis of the muscle active section, and produce the second feature vector by arithmetically operating conversion values of a roll angle, a pitch angle, and a yaw angle of the inertial measurement unit on a basis of the motion section and then applying a high-pass filter.

7. The sign language recognition system of claim 2, wherein the first feature vector and the second feature vector are resampled by normalizing time data.

8. The sign language recognition system of claim 1, wherein the search unit performs the search using a neural network formed through learning of a specific sign language gesture.

9. The sign language recognition system of claim 1, wherein
the inertial measurement unit includes a three-axis accelerometer, a three-axis angular velocity sensor, and a three-axis magnetometer.

10. A sign language recognition method, comprising:
wearing a sensor measurement device around an arm of a user, wherein the sensor measurement device includes: an armband worn around the arm; multiple electrodes arranged at intervals along an inner circumference of the armband and associated with multiple electrode channels, respectively; and an inertial measurement unit provided in an area of the sensor measurement device;
acquiring an electromyogram signal through multiple electrode channels according to a gesture of straightening a wrist of the user, identifying an electrode channel having a maximum root mean square value among the multiple electrode channels on a basis of the electromyogram signal, and rearranging the multiple electrode channels in consideration of a position of the identified electrode channel, wherein the position of the identified electrode channel is a position corresponding to a position of a wrist extensor bundle;

extracting a muscle active section from the electromyogram signal to detect a sign language gesture of the user;

producing a first feature vector by performing signal processing to the muscle active section;

searching a signal corresponding to the first feature vector in a database; and outputting a text corresponding to the searched signal.

11. The sign language recognition method of claim 10, further comprising: acquiring an inertial signal from the inertial measurement unit, extracting a motion section of the arm from the inertial signal, producing a second feature vector by performing signal processing to the motion section, and searching a signal corresponding to an integrated feature vector in the database, wherein the integrated feature vector is obtained by integrating the first feature vector and the second feature vector.

12. The sign language recognition method of claim 11, further comprising: computing an orientation initial value of the inertial measurement unit and an orientation value of the inertial measurement unit according to real-time receipt of the inertial signal using the acquired inertial signal; and arithmetically operating conversion values of a roll angle, a pitch angle, and a yaw angle of the inertial measurement unit using a reference vector determined on the basis of the orientation initial value and a movement vector determined on the basis of the orientation value.

13. The sign language recognition method of claim 11, wherein a Teager-Kaiser Energy Operator (TKEO) is applied to the electromyogram signal and the inertial signal to extract the muscle active section and the motion section.

14. The sign language recognition method of claim 11, further comprising: extracting a section having a predetermined muscle activity threshold value from the electromyogram signal as the muscle active section and a section having a predetermined motion threshold value from the inertial signal as the motion section.

15. The sign language recognition method of claim 11, wherein
the first feature vector is produced by arithmetically operating a root mean square value of the electromyogram signal for the respective multiple electrode channels on a basis of the muscle active section; and
the second feature vector is produced by arithmetically operating conversion values of a roll angle, a pitch angle, and a yaw angle of the inertial measurement unit on a basis of the motion section and then applying a high-pass filter.

16. The sign language recognition method of claim 11, wherein the first feature vector and the second feature vector are resampled by normalizing time data.

17. The sign language recognition method of claim 10, wherein the searching includes: performing the search using a neural network formed through learning of a specific sign language gesture.

18. The sign language recognition method of claim 10, wherein
the inertial measurement unit includes a three-axis accelerometer, a three-axis angular velocity sensor, and a three-axis magnetometer.

19. A non-transitory computer-readable storage medium that stores a program configured to execute a method of claim 10 on a computer.

* * * * *